US008741645B2

(12) United States Patent
Hattori et al.

(10) Patent No.: US 8,741,645 B2
(45) Date of Patent: Jun. 3, 2014

(54) TEST KIT COMPRISING A CULTURE INSTRUMENT WITH A CELL PATTERN AND A GEL SUITABLE TO EMBED CELL PATTERN

(75) Inventors: Hideshi Hattori, Tokyo (JP); Norihiko Okochi, Tokyo (JP); Masatoshi Kuroda, Tokyo (JP); Masahiko Hase, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 13/092,552

(22) Filed: Apr. 22, 2011

(65) Prior Publication Data

US 2011/0201116 A1 Aug. 18, 2011

Related U.S. Application Data

(62) Division of application No. 11/936,836, filed on Nov. 8, 2007, now Pat. No. 8,592,139.

(30) Foreign Application Priority Data

Nov. 10, 2006 (JP) ................................ 2006-305769

(51) Int. Cl.
*C12N 5/02* (2006.01)
*C12N 5/07* (2010.01)
*A61K 9/60* (2006.01)
*A01N 63/02* (2006.01)
*A61K 9/62* (2006.01)
*A61K 9/64* (2006.01)

(52) U.S. Cl.
USPC ......... 435/395; 424/93.21; 424/488; 424/499

(58) Field of Classification Search
USPC ........................ 435/395; 424/93.21, 488, 499
See application file for complete search history.

(56) References Cited

U.S. PATENT DOCUMENTS

| 5,470,739 | A | 11/1995 | Akaike et al. |
| 6,133,030 | A | 10/2000 | Bhatia et al. |
| 6,221,663 | B1 | 4/2001 | Bhatia et al. |
| 2002/0095219 | A1 | 7/2002 | Nelles et al. |
| 2007/0259328 | A1 | 11/2007 | Morita et al. |

FOREIGN PATENT DOCUMENTS

| EP | 1428871 A1 | 6/2004 |
| JP | 3-007576 A | 1/1991 |
| JP | 5-176753 A | 7/1993 |
| JP | 2777392 B2 | 5/1998 |
| JP | 2005342112 A | 12/2005 |
| WO | 0107891 A2 | 2/2001 |
| WO | 03/010302 A1 | 2/2003 |

OTHER PUBLICATIONS

Tang et al. 2003. Molding of Three-Dimensional Microstructures of Gels. Journal of American chemical Society, vol. 125, pp. 12988-12989.*
Peterbauer et al. 2006. Simple and versatile methods for the fabrication of arrays of live mammalian cells. Lab Chip, vol. 6, pp. 857-863.*
Curtis et al. 1983. Adhesion of Cells to Polystyrene Surfaces. The Journal of Cell Biology, vol. 97, pp. 1500-1506.*
Anton et al. The EFSA Journal (2005), vol. 294, pp. 1-15.*
Köster et al. 2006. Microbiosensors for Measurement of Microbially Available Dissolved Organic Carbon: Sensor Characteristics and Preliminary Environmental Application. Applied and Environmental Microbiology, vol. 72, No. 11, Nov. 2006, pp. 7063-7073; Published Ahead of Print Aug. 25, 2006.*
Dirk R. Albrecht, et al.; "Probing the Role of Multicellular Organization in Three-Dimensional Microenvironments", Nature Methods, pp. 369-375; May 2006; vol. 3, No. 5.
Francois Berthiaume, et al.; "Effect of Extracellular Matrix Topology on Cell Structure, Function, and Physiological Responsiveness: Hepatocytes Cultured in a Sandwich Configuration"; The FASEB Journal; 1996; pp. 1471-1484; vol. 10.
John O. Connolly, et al.; "Rac Regulates Endothelial Morphogenesis and Capillary Assembly", Molecular Biology of the Cell: Jul. 2002; pp. 2474-2485; vol. 13.
Craig K Griffith. M.S., et al.; "Diffusion Limits of an in Vitro Thick Prevascularized Tissue"; Tissue Engineering; 2005; pp. 257-266; vol. 11. No. 1/2.
Thomas Korff, et al.; "Blood Vessel Maturation in a 3-Dimensional Spheroidal Coculture Model: Direct Contact with Smooth Muscle Cells Regulates Endothelial Cell Quiescence and Abrogates VEGF Responsiveness"; The FASEB Journal; 2001; pp. 447-457; vol. 15.
Takehisa Matsuda, et al.; "Control of Cell Adhesion, Migration and Orientation on Photochemically Microprocessed Surfaces"; Journal of Biomedical Materials Research; 1996; pp. 165-173; vol. 32; John Wiley & Sons.
Xingyu Jiang, et al; "Directing Cell Migration with Asymmetric Micropatterns"; Proceedings of the National Academy of Sciences; Jan. 25, 2005; pp. 975-978; vol. 102, No. 4.
Celeste M Nelson, et al.; "Emergent Patterns of Growth Controlled By Multicellular Form and Mechanics"; Proceedings of the National Academy of Sciences; Aug. 16, 2005; pp. 11594-11599, vol. 102, No. 33.
Moo-Yeal Lee, et al.; "Metabolizing Enzyme Toxicology Assay Chip (MetaChip) for High-throughput Microscale Toxicity Analyses"; Proceedings of the National Academy of Sciences; Jan. 25, 2005: pp. 983-987; vol. 102, No. 4.

(Continued)

*Primary Examiner* — Jon P Weber
*Assistant Examiner* — Kailash C Srivastava
(74) *Attorney, Agent, or Firm* — Sughrue Mion, PLLC

(57) ABSTRACT

The present invention provides a method for performing a biological test under conditions in which an artificially prepared cell pattern with initial position coordinates that can be determined is three-dimensionally cultured within a gelled matrix. The present invention relates to a biological test method that comprises testing a biological indicator with reference to at least one selected from the group consisting of cell proliferation, cell movement, and cell differentiation in a cell pattern substantially embedded in gel. The present invention also relates to a kit for the biological test method.

5 Claims, 6 Drawing Sheets

(56) References Cited

OTHER PUBLICATIONS

Yu-Suke Torisawa, et al.; "Multi-channel 3-D Cell Culture Device integrated on a Silicon Chip for Anticancer Drug Sensitivity Test": Biomaterials: May 2005; pp. 2165-2172; vol. 26, No. 14; Elsevier Science Publishers BV.

Albert Folch, et al.; "Microfabricated Elastomeric Stencils for Micropatterning Cell Cultures"; Journal of Biomedical Material Research; 2000; pp. 346-353; John Wiley & Sons, Inc.

Temitope R. Sodunke, et al; "Micropatterns of Matrigel for Three-Dimensional Epithelial Cultures"; Biomaterials; Sep. 2007; pp. 4006-4016; vol. 28, No. 27, Elsevier Science Publishers BV.

"Reports on Outcomes of Research Grant Projects"Japan Cardiovascular Research Foundation: 2000.

Ostuni et al., "Patterning Mammalian Cells Using Elastomeric Membranes"; Langmuir: 2000; pp. 7811-7819: vol. 16.

Sodunke et al.; "Micropatterns of Matrigel for three dimensional epithelial cultures "; Biomaterials; 2007; pp. 4006-4016; vol. 28.

* cited by examiner

TEST KIT COMPRISING A CULTURE INSTRUMENT WITH A CELL PATTERN AND A GEL SUITABLE TO EMBED CELL PATTERN

CROSS REFERENCE TO RELATED APPLICATION

This application is a Divisional of application Ser. No. 11/936,836 filed Nov. 8, 2007, which is based on Japanese Patent Application No. 2006-305769 filed on Nov. 10, 2006, the disclosure of which is incorporated herein by reference in its entirety.

BACKGROUND OF THE INVENTION

1. Field of the Invention

The present invention relates to a biological test method using cells, which is used in the fields involving pharmaceuticals, medical care, foods, medicine, pharmacy, biology, and the like. The present invention particularly relates to a biological test method using three-dimensional culture considered to enable obtainment of information that is more useful than that obtained via conventional two-dimensional culture. The biological test method is technology that is worthwhile as an alternative to animal testing.

2. Background Art

In recent years, lower investment efficiency in research and development has become an issue in the pharmaceutical industry. Hence, biological test methods using three-dimensional culture methods are attracting attention as methods useful for reducing the high costs of animal experimentation. Such biological test methods using three-dimensional culture methods are expected to be useful for obtainment of basic data that enable in vivo prediction of the absorption, distribution, metabolism, excretion, and toxicity of new drugs in particular. This technology will influence not only the pharmaceutical industry, but also on treatment and diagnosis in the fields of medical care, food safety tests, and the like. Also, rapidly developed from research using a conventional two-dimensional culture method is research using a combination of cellular imaging technology and a three-dimensional culture method. Practical use of screening technology that constitutes a combination of cellular imaging technology and a three-dimensional culture method has already been initiated.

A conventional three-dimensional culture method will be described below. The most simple three-dimensional culture method involves culturing cells dispersed in a gel matrix such as collagen or agarose gel in an appropriate container. Furthermore, a method that involves forming a gel layer on the bottom of a culture container, seeding cells on the bottom, and then culturing the cells is also regarded as a three-dimensional culture method when the cells migrate or infiltrate into the gel. Non-patent Document 1 discloses a method, namely a sandwich culture method that involves forming a gel layer on the bottom of a culture container, seeding cells on the gel layer, culturing the cells, removing medium after a predetermined time period, adding a gel precursor onto the cell layer for gelling, and then further culturing the resultant. Furthermore, Non-patent Document 2 discloses a method that involves forming a gel layer on a general two-dimensional culture cells and then performing a test. Non-patent Document 3 discloses a method that involves previously culturing cells on the surfaces of beads, embedding them within a gel matrix, and then performing a test. Moreover, Non-patent Document 4 discloses a method that involves embedding cell spheroids within a gel matrix and then performing a test.

These three-dimensional culture methods are attracting attention concerning the culture of a plurality of cell types; that is, coculture. That is because cell behavior more analogous to that observed in vivo can be expected with the use of coculture compared with culture of a single cell type.

However, these methods are problematic in that the initial position coordinates of single cells or cell aggregates cannot be specified and control of the distribution of cell aggregate sizes is difficult. Hence, application of these methods to an advanced biological test system using a combination of robotics and viable cell analysis techniques has been limited. The use of the method disclosed in Non-patent Document 4 basically addresses the above problems since one spheroid is formed in each well of a formatted well plate. However in this case, a plurality of spheroids cannot be cultured with determined position coordinates thereof in each well, so that obtainment of a plurality of data from each well and statistical data analysis cannot be performed. Furthermore, a method must be employed to observe spheroids being embedded in gel under a microscope, which involves harvesting one spheroid prepared per well of a well plate and then dispersing it for casting in a solution before gelling. Furthermore, the form of a cell aggregate that can be used in the method disclosed in Non-patent Document 4 is limited to a spheroid.

Meanwhile, in recent years, the field of research using a combination of a fine processing technology such as semiconductor technology or printing technology and biotechnology has been significantly developed. There are great expectations for this research, since it may lead to development of new healthcare technology or production of efficient drug discovery tools. For example, as disclosed in Non-patent Document 5, Patent Document 1, Patent Document 2, and Patent Document 3, it has been reported that a culture instrument is produced via application of technology for lithographying a photosensitive polymeric material (photoresist) or the like, so as to obtain a two-dimensional cell pattern. Furthermore, Patent Document 4 and Patent Document 5 disclose technology that realizes a two-dimensional co-culture system through combination with a step of removing a photoresist, so as to use the system for a cell function test. Recently, technology for preparing a two-dimensional cell pattern through application of coating with a thickness at the molecular level and the application of such technology have been reported. Non-patent Document 6 discloses technology for testing cell movement with the use of a cell pattern having a cell having an artificially controlled adhesion mode as a component. Moreover, Non-patent Document 7 discloses technology for testing cell proliferation activity or the like using an artificial cell pattern containing cell aggregates as components or using a cell sheet that is formed on an instrument having artificial geometric up and down. Furthermore, Non-patent Document 8 reports a test method that is not an example of using a cell pattern and involves causing a microgel array on which a metabolism enzyme is complexed with a chemical substance to come into contact with monolayered culture cells, following which the toxicity of a metabolite produced by the metabolism enzyme is tested.

Among these examples of technology, a general method using a polymer resist (Non-patent Document 5, Patent Document 1, Patent Document 2, or Patent Document 3) often leads to the production of cell movement test systems differing from general two-dimensional culture, since the resist generally has a degree of thickness that hinders cell movement. The resulting test systems are often considered to be troublesome artificial test systems and they have failed to attract attention in application fields such as pharmacological tests. In the meantime, the above problem concerning such resist thickness has been addressed in Patent Document 4, Patent Document 5, Non-patent Document 6, and Non-patent Document 7. However, these documents do not mention any biological test method that involves culturing an artificial single cell pattern or a cell aggregate pattern in a matrix. Technology disclosed in Non-patent Document 8 is expected as a new high-throughput pharmacological test method. However, this is not appropriate as a test method for testing parameters concerning single cell or cell aggregate movement.

Furthermore, technology that is a combination of fine processing technology and three-dimensional culture has been recently reported. Patent Document 6 discloses a method for preparing a spheroid pattern comprising artificially prepared vascular endothelial cells and hepatic cells and the use of the method. Non-patent Document 9 discloses technology that involves artificially and three-dimensionally aligning cells in a matrix before gelling and then gelling the matrix. Moreover, Patent Document 7 discloses a method for preparing artificial tissue, which involves transferring a cell layer prepared via pattern culture to a complex composed of a cell layer and a basal membrane layer, so as to prepare artificial tissue. Non-patent Document 10 discloses a method that involves pattern culturing cells on collagen gel using a stencil mask, removing the stencil mask, placing a collagen solution on the cell pattern for gelling, and then sandwich culturing the patterned cells. Furthermore, Non-patent Document 11 discloses technology that involves preparing a polymer pattern through laser ablation, pattern culturing vascular endothelial cells, transferring the cell pattern onto gel, forming gel on the transferred cell pattern, and performing three-dimensional culture.

However, Patent Document 6 does not disclose any biological test method that involves three dimensional culturing of an artificially prepared single cell pattern or cell aggregate pattern in a gelled matrix. Non-patent Document 9 discloses technology for culturing a cell pattern artificially prepared in gel, but does not disclose any method for testing a biological indicator concerning the movement of single cells or cell aggregates prepared in an artificial pattern in a gel matrix. Patent Document 7, Non-patent Document 10, and Non-patent Document 11 disclose three-dimensional culture technology for cell aggregates prepared in an artificial pattern. However, these inventions are not intended for performance of biological tests for parameters concerning the movement or the proliferation of cell aggregates, and they disclose almost nothing concerning such parameters. Furthermore, according to Patent Document 7 and Non-patent Document 11, transfer of cells from a hard culture instrument requires approximately 24 hours. This suggests that cells strongly interact with such a hard culture instrument. Hence, technology according to Patent Document 7 and Non-patent Document 11 is problematic in that it is likely to be recognized as a culture system that includes artificial factors, compared with conventional three-dimensional culture technology. Moreover, the method according to Non-patent Document 10 is problematic in that freedom to design a cell pattern is limited since use of a stencil mask is an essential requirement.

Patent Document 1 JP Patent Publication (Kokai) No. 3-7576 A (1991)
Patent Document 2 JP Patent Publication (Kokai) No. 5-176753 A (1993)
Patent Document 3 JP Patent No. 2777392
Patent Document 4 U.S. Pat. No. 6,133,030
Patent Document 5 U.S. Pat. No. 6,221,663
Patent Document 6 WO2003/010302
Patent Document 7 JP Patent Publication (Kokai) No. 2005-342112 A
Non-patent Document 1 The FASEB Journal, vol. 10, 1471-1484 (1996)
Non-patent Document 2 Molecular Biology of the Cell, vol. 13, 2474-2485 (2002)
Non-patent Document 3 Tissue Engineering, vol. 11, no. 1/2, 257-266 (2005)
Non-patent Document 4 The FASEB Journal, vol. 15, 447-457 (2001)
Non-patent Document 5 Journal of Biomedical Materials Research, vol. 32, 165-173 (1996)
Non-patent Document 6 Proceedings of the National Academy of Sciences, vol. 102, no. 4, 975-978 (2005)
Non-patent Document 7 Proceedings of the National Academy of Sciences, vol. 102, no. 33, 11594-11599 (2005)
Non-patent Document 8 Proceedings of the National Academy of Sciences, vol. 102, no. 4, 983-987 (2005)
Non-patent Document 9 Nature Methods, vol. 3, no. 5, 369-375 (2006)
Non-patent Document 10 Journal of Biomedical Material Research, vol. 52, 346-353 (2000)
Non-patent Document 11 Report of Research Support 2000 (ISSN 0916-3719) Japan Cardiovascular Research Foundation

SUMMARY OF THE INVENTION

The present invention provides a biological test method using culture cells and a test kit for the method, neither of which have been sufficiently achieved by the above known technologies. Specifically, the present invention provides a method for performing a biological test under conditions in which a cell pattern comprising artificially prepared single cells or cell aggregates, the initial position coordinates of which can be determined, is three-dimensionally cultured within a gelled matrix or a condition in which such cell pattern is pseudo-three-dimensionally cultured using a culture instrument that weakly interacts with cells and a gelled matrix. In particular, the present invention provides a method for testing parameters concerning the movement of a single cell or a cell aggregate. The present invention further provides a test kit that is suitable for realization of such method.

The term "cell aggregate (cell population)" in this specification is defined as follows. The term "cell aggregate (cell population)" refers to a condition in which a plurality of cells aggregate through some cell-to-cell adhesion at least in the early phase of three-dimensional culture in a test. In addition, it goes without saying that cell-to-cell adhesion may change over the course of a test.

The present invention encompasses the following (1) to (14).

(1) A biological test method, comprising testing a biological indicator with reference to at least one selected from the group consisting of cell proliferation, cell movement, and cell differentiation in a cell pattern substantially embedded in gel.
(2) The biological test method according to (1), wherein the cell pattern is entirely embedded in gel, a portion of the cell pattern is exposed and the remaining portion is embedded in gel, or a portion of the cell pattern is in contact with a solid substrate and the remaining portion is embedded in gel.
(3) The biological test method according to (1) or (2), wherein the gel is gel containing at least one type of protein contained in an extracellular matrix, gel containing a pseudo-extracellular matrix, a cell sheet, or a complex thereof.
(4) The biological test method according to any one of (1) to (3), wherein another cell is present in the gel.

(5) The biological test method according to any one of (1) to (4), wherein the cell pattern substantially embedded in the gel is formed by a method that involves performing cell culture on a culture instrument having a culture surface on which a cell pattern can be formed and then coating the culture surface with the gel after culture.

(6) The biological test method according to (5), wherein the cell pattern substantially embedded in the gel is formed by a method that involves performing cell culture on a culture instrument having a culture surface on which a cell pattern can be formed, coating the culture surface with the gel after culture, transferring the cell pattern into the gel, and then peeling off the culture instrument.

(7) The biological test method according to (6), wherein the cell pattern substantially embedded in the gel is formed by a method that involves performing cell culture on a culture instrument having a culture surface on which a cell pattern can be formed, coating the culture surface with the gel after culture, transferring the cell pattern into the gel, peeling off the culture instrument, and then further coating with gel the face from which the culture instrument on the gel has been peeled off.

(8) The biological test method according to any one of (5) to (7), wherein the culture surface of the culture instrument is provided with a cell adhesion region and a cell-adhesion-inhibiting region, the cell adhesion region is formed with a film prepared to have cell adhesion properties by subjecting a cell-adhesion-inhibiting hydrophilic film containing an organic compound having a carbon-oxygen bond to oxidation treatment and/or degradation treatment, and the cell-adhesion-inhibiting region is formed with a hydrophilic film containing an organic compound having a carbon-oxygen bond.

(9) The biological test method according to any one of (5) to (7), wherein the culture surface of the culture instrument is provided with a cell adhesion region and a cell-adhesion-inhibiting region, the cell adhesion region and the cell-adhesion-inhibiting region are each formed with a hydrophilic film containing an organic compound having a carbon-oxygen bond, and the density of the organic compound in the cell adhesion region is lower than that of the organic compound in the cell-adhesion-inhibiting region.

(10) The biological test method according to any one of (5) to (9), wherein the culture surface of the culture instrument is provided with a cell adhesion region and a cell-adhesion-inhibiting region and a difference in height between these regions is 10 nm or less.

(11) A biological test kit, comprising a culture instrument having a culture surface on which a cell pattern can be formed and gel.

(12) The biological test kit according to (11), wherein the culture surface of the culture instrument is provided with a cell adhesion region and a cell-adhesion-inhibiting region and the cell adhesion region is formed with a film prepared to have cell adhesion properties by subjecting a cell-adhesion-inhibiting hydrophilic film containing an organic compound having a carbon-oxygen bond to oxidation treatment and/or degradation treatment, and the cell-adhesion-inhibiting region is formed with a hydrophilic film containing an organic compound having a carbon-oxygen bond.

(13) The biological test kit according to (11), wherein the culture surface of the culture instrument is provided with a cell adhesion region and a cell-adhesion-inhibiting region, the cell adhesion region and the cell-adhesion-inhibiting region are each formed with a hydrophilic film containing an organic compound having a carbon-oxygen bond, and the density of the organic compound in the cell adhesion region is lower than that of the organic compound in the cell-adhesion-inhibiting region.

(14) The biological test kit according to any one of (11) to (13), wherein the culture surface of the culture instrument is provided with a cell adhesion region and a cell-adhesion-inhibiting region and a difference in height between these regions is 10 nm or less.

EFFECT OF THE INVENTION

The present invention makes it possible to culture cell aggregates having position coordinates that can be determined and having an arbitrary size such that there are almost the same numbers of cells in the cell aggregates in a gelled matrix or under an environment equivalent to such a matrix. In particular, the present invention makes it possible to realize biological tests involving high-level three-dimensional culture, such as a vascularization test with better quantitative capability than conventional methods, a vascular remodeling test that involves simulation of in vivo vascular development or vascularization, a pharmacological test for a compound that inhibits the migration or infiltration of individual cells or cell aggregates, a test concerning epithelium-stroma transfer (and, in particular, epithelium-stroma transfer of cell aggregates), a test concerning the metastasis of cancer tissue, an artificial matrix performance test using model cells, and the like.

This description includes part or all of the contents as disclosed in the description and/or drawings of Japanese Patent Application No. 2006-305769, which are priority documents of the present application.

Figure 1:
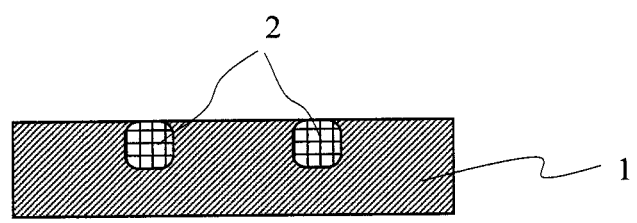
FIG. 1 shows a cross-sectional view of a test system comprising cell patterns (2), wherein most of each cell pattern is embedded in gel layer (1) and partially exposed.

EXPLANATION OF REFERENCE NUMERALS 1, 3, 5, 7, 9, 10, 13, and 16 . . . Gel layer
2, 6, 8, 11, 12, and 14 . . . Cell patterns 4 . . . Solid substrate (culture instrument)
15 . . . Substance to be tested
L . . . Distance between cell pattern (14) and substance to be tested (15)

DETAILED DESCRIPTION OF THE PREFERRED EMBODIMENTS (Cell Pattern)

Figure 6:
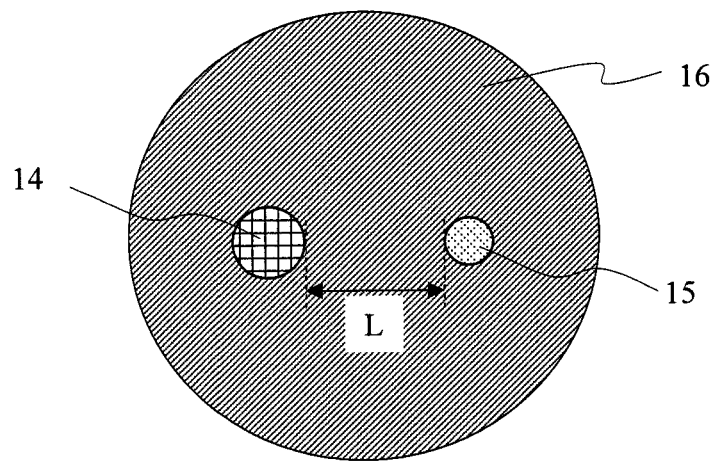
FIG. 6 shows a plan view of a test system, wherein a cell pattern (14) and a substance (15) to be tested in terms of effect on the cell pattern are positioned and arranged within gel layer (16).

In the present invention, "cell pattern" refers to a pattern formed with single cells or cell aggregates that are artificially positioned and arranged. Initial artificial positioning of cells makes it possible to specify the position coordinates of cells or cell aggregates at the start of a biological test. Furthermore, initial artificial positioning of cells facilitates microscopic observation and makes it possible to perform statistical data analysis. Moreover, cell patterns can be prepared to have any sizes. Cell aggregates can be prepared so that they are all composed of almost the same number of cells, while minimizing the variation in such number. Furthermore, a plurality of cells or cell aggregates can be arranged at any intervals, facilitating observation of interaction between a plurality of cells or cell aggregates arranged at intervals according to the relevant test content. Furthermore, the position coordinates of a cell pattern can be determined. Accordingly, distance L between a substance to be tested (15) and a cell pattern (14) that comprises cells or cell aggregates as shown in FIG. 6 is arbitrarily determined using a commercially available spotter or the like. Hence, local arrangement of the substance to be tested (15) in gel (16) is also facilitated. Examples of such cell pattern include a cell pattern in which single cells or spheroids (spherical cell aggregates) are arranged at predetermined coordinates, a cell pattern in which a plurality of single cells or spheroids are arranged at predetermined intervals, and a cell pattern in which cell aggregates are arranged so as to form a predetermined shape such as a line, tree, a network, a lattice, a circle, or a quadrangle. A cell pattern formed with cell aggregates may be one-dimensionally-shaped, two-dimensionally-shaped, or three-dimensionally-shaped. An example of a one-dimensional cell pattern is a cell pattern formed with cell aggregates wherein cells are linearly aligned. An example of a two-dimensional cell pattern is a cell pattern formed with planar cell aggregates that are formed with skin epidermal cells, for example. An example of a three-dimensional cell pattern is a cell pattern formed with spheroids, tubular cell aggregates that are formed with, vascular endothelial cells, or the like. Furthermore, two-dimensional cell aggregates can be multilayered to compose a three-dimensional cell pattern. In addition, a one-dimensional or a two-dimensional cell pattern may grow or become deformed three-dimensionally within gel so as to compose a three-dimensional cell pattern.

Cells composing a cell pattern can be adequately selected according to the purpose of a test. In particular, mammalian cells having adhesion property are useful. Suspended cells such as leukocytes can also be used in a system where appropriate ligands and cells coexist. Examples of mammalian species from which cells are derived include mice, rats, monkeys, dogs, pigs, and humans. Furthermore, cells composing a cell pattern may be normal cells represented by primary cells, abnormal (pathological) cells represented by primary cells or cells of established cell lines obtained from the malignant tumor of a patient, or cells of established cell lines that have acquired infinite proliferation ability in the course of subculture of normal cells. Cells composing a cell pattern may be embryonic stem cells, multipotent stem cells, precursor cells having limited differentiation ability, or differentiated cells that have completed differentiation. Origins of organs are not particularly limited. Examples of such cells derived from organs include hepatic cells that are hepatic parenchymal cells, Kupffer cells, endothelial cells such as vascular endothelial cells and corneal endothelial cells, fibroblasts, osteoblasts, osteoclasts, cells derived from periodontal ligament, epidermal cells such as epidermal keratinocytes, epithelial cells such as tracheal epithelial cells, gastrointestinal epithelial cells, cervical epithelial cells, corneal epithelial cells, and mammary gland epithelial cells, and pericytes, muscle cells such as smooth muscle cells and cardiac muscle cells, renal cells, islets of Langerhans cells, nerve cells such as peripheral neuronal cells and optic nerve cells, chondrocytes, and bone cells. In addition, a single type of cell may be cultured or two or more types of cell may be co-cultured.

Another test system that maximizes exertion of the characteristics of the present invention is employed to conduct a three-dimensional culture test that uses cell aggregates each consisting of two or more cells having cell-to-cell binding as an element of a cell pattern while maintaining the cell-to-cell binding as far as possible.

Another test system that is thought to maximize exertion of the characteristics of the present invention is employed when an in vitro three-dimensional culture system is used to test cell aggregates in terms of motility or morphological changes involved in cancer metastasis, such as Epithelial-Mesenchymal Transition (EMT).

Another test system that is thought to maximize exertion of the characteristics of the present invention is employed when the distance between cell aggregates and a substance to be tested in gel or the distance between cell aggregates and another cell type (interaction between them is to be observed) is determined and then a three-dimensional culture test is performed.

(Gel)

Gel to be used in the present invention is not particularly limited, as long as a cell pattern embedded therein can exert functions such as proliferation, movement, and differentiation. Specific examples of such gel include artificial hydrogel such as a hydrophilic polymer (e.g., polyacrylic acid, polyvinyl alcohol, and polyethylene glycol) and hydrogel made of a synthetic substance such as an artificial peptide (e.g., PuraMatrix (trademark)). Further examples of the same include gel made of polysaccharides such as gel made of hyaluronic acid or a derivative thereof used therein, and gel made of dextran or a derivative thereof used therein. An example of gel made of protein is gel made of various types of collagen, gelatin, fibrin gel, or the like. An example of a special extracellular matrix is gel made of a biological site-specific protein such as a basal membrane represented by Matrigel (trademark). Furthermore, gel made of these complexes can also be used. Among these types of gel, gel containing an organism-derived raw material as an element is desired. Many biological test case examples concerning such gel have been accumulated, so that individual test methods to which the present invention is applied can be developed based on the case examples. Cross-linking reaction for gelling may be physical, chemical, or physical and chemical reaction. Gel made of an artificial peptide is also preferable. This is because: gel can be produced by total synthesis; and it is expected that the quality (e.g., biological activity and gelling ability) of such gel can be easily controlled so as to improve reproducibility in a test. Furthermore, in the present invention, a cell sheet that can be said to be living gel is also applicable. When necessary, another cell may also be present in gel and a drug for a test may also be contained.

(Embedding of Cell Pattern in Gel)

Figure 2:
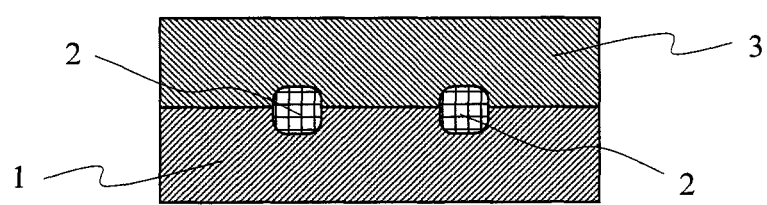
FIG. 2 shows a cross-sectional view of a test system comprising cell patterns (2), wherein the cell patterns (2) are arranged between two gel layers (1) and (3) and are entirely embedded in gel.
Figure 3:
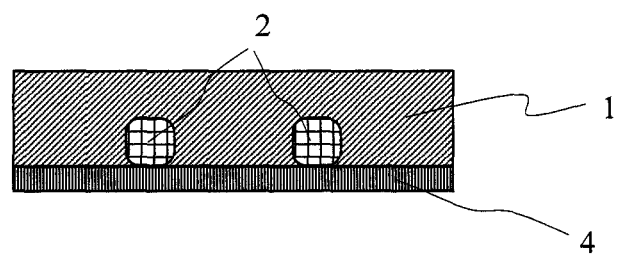
FIG. 3 shows a cross-sectional view of a test system comprising cell patterns (2), wherein each cell pattern is partially in a contact with solid substrate (4) and the remaining portion thereof is embedded in gel layer (1).
Figure 4:
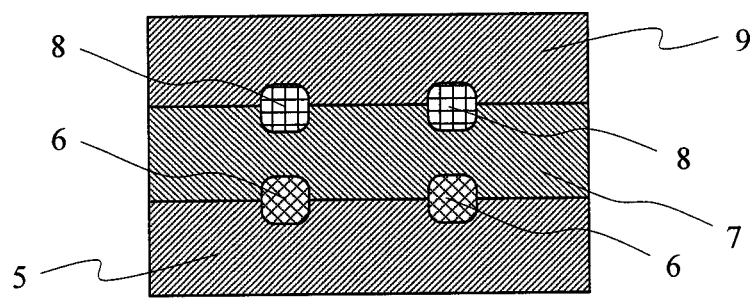
FIG. 4 shows a cross-sectional view of a test system comprising cell patterns (6) and cell patterns (8) that are arranged via lamination, wherein each cell pattern (6) is arranged between two gel layers (5) and (7) and is entirely embedded within gel and each cell pattern (8) is arranged between two gel layers (7) and (9) and is entirely embedded in gel.
Figure 5:
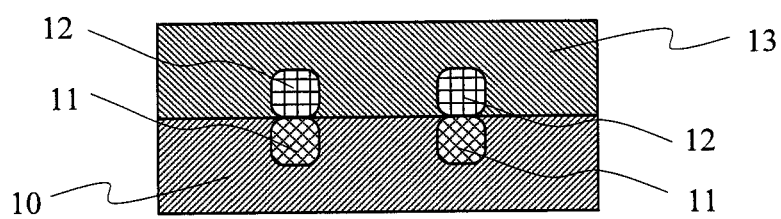
FIG. 5 shows a cross-sectional view of a test system, wherein most of each cell pattern (11) is embedded in gel layer (10), most of each cell pattern (12) is embedded in gel layer (13), and each cell pattern (11) is arranged to face each cell pattern (12) so that they come into contact with each other.

The present invention is characterized in that a cell pattern is substantially embedded in gel. The phrase "substantially embedded in gel" means that a portion of a cell pattern may be exposed or in contact with a portion other than gel so as not to affect the functions of the cell pattern, such as proliferation, movement, and differentiation. Specifically, the test method of the present invention can be performed under conditions in which a cell pattern is entirely embedded in gel. In addition to such conditions, the test method can also be performed under conditions in which a portion of a cell pattern is exposed in liquid medium other than gel or air or under conditions in which a cell pattern is in contact with a solid substrate, so as not to affect the functions of the cell pattern. FIGS. 1 to 5 show typical examples of the test system of the present invention. FIG. 1 shows a cross-sectional view of a test system comprising cell patterns (2) wherein most of each cell pattern is embedded in gel layer (1) and partially exposed to the peripheral culture solution or the like. FIG. 2 shows a cross-sectional view of a test system comprising cell patterns (2), wherein the cell patterns (2) are arranged two gel layers (1) and (3) and are entirely embedded in gel. FIG. 3 shows a cross-sectional view of a test system comprising cell patterns (2), wherein each cell pattern is partially in contact with solid substrate (4) and the remaining portion thereof is embedded in gel layer (1). FIG. 4 shows a cross-sectional view of a test system comprising cell patterns (6) and cell patterns (8) that are arranged via lamination, wherein each cell pattern (6) is arranged between two gel layers (5) and (7) and is entirely embedded in gel and each cell pattern (8) is arranged between two gel layers (7) and (9) and is entirely embedded in gel. FIG. 5 shows a cross-sectional view of a test system, wherein most of each cell pattern (11) is embedded in gel layer (10), most of each cell pattern (12) is embedded in gel layer (13), and cell pattern (11) is arranged to face cell pattern (12) so that they come into contact with each other. When a cell pattern is entirely embedded in gel, cells composing the cell pattern can be three-dimensionally cultured. Moreover, even when a portion of a cell pattern is exposed or in contact with a portion other than gel so as not to affect the functions of cell proliferation, cell movement, cell differentiation, and the like, substantial three-dimensional culture can be performed. A culture solution appropriate for cell culture or a buffer appropriate for a biological test may be present inside or in the periphery of gel.

A cell pattern can be embedded into gel by the following procedures. Cells are seeded on the culture surface of a culture instrument having a culture surface on which a cell pattern can be formed. Cells are then cultured, a cell pattern is formed on the culture surface, and then the culture surface is coated with a gel layer. Hence, as shown in FIG. 3, cell patterns (2) that are partially in contact with solid substrate (4) and the remaining portions are embedded in gel layer (1) are obtained. Furthermore when cell patterns (2) are transferred into gel layer (1) and then culture instrument (solid substrate) (4) is peeled off, cell patterns (2) with portions exposed as shown in FIG. 1 and with the remaining portions embedded in gel layer (1) are obtained. Furthermore, when the surface of gel layer (1) from which the culture instrument is peeled off is coated with gel layer (3), cell patterns (2) embedded in two gel layers (1) and (3) are obtained as shown in FIG. 2. Furthermore, the test systems in FIGS. 4 and 5 can be produced with the use of similar steps. When two or more gel layers are used, gel layers may be of the same type or different types and the interface between the layers may be clear or unclear.

(Culture Instrument)

A culture instrument to be used for obtaining an artificial cell pattern has a culture surface on which cells are arranged in a predetermined pattern. Such culture surface is typically provided with cell adhesion regions and cell-adhesion-inhibiting regions, on which cells or cell aggregates are patterned along the shape or the arrangement of such cell adhesion regions. Examples of materials for such cell adhesion regions include synthetic polymers such as polystyrene, polyester, and a silicone resin, glass, metals such as gold and titanium, hydrophilic synthetic polymers to which cell adhesion property is imparted to some extent, such as denatured polyacrylamide, denatured polyacrylic acid, denatured polyethylene glycol, and denatured polyvinyl alcohol. Examples of materials for such cell-adhesion-inhibiting regions include polyacrylic acid, polyethylene glycol, Pluronics (registered trademark), polyacrylamide, polyvinyl alcohol, agar, and albumin. More preferred embodiments of such a cell adhesion region and cell-adhesion-inhibiting region are as explained below.

There are two typical embodiments of the culture surface provided with cell adhesion regions and cell-adhesion-inhibiting regions. In a first embodiment: cell adhesion regions are each formed with a film prepared by subjecting a cell-adhesion-inhibiting hydrophilic film containing an organic compound having a carbon-oxygen bond to oxidation treatment and/or degradation treatment, so as to impart cell adhesion properties to the resulting film; and cell-adhesion-inhibiting regions are each formed with a hydrophilic film containing an organic compound having a carbon-oxygen bond. In a second embodiment: cell adhesion regions and cell-adhesion-inhibiting regions are each formed with a hydrophilic film containing an organic compound having a carbon-oxygen bond so that density of the organic compound in the cell adhesion region is lower than density of the organic compound in the cell-adhesion-inhibiting region. Both embodiments are adequate for the present invention but particularly the first embodiment is preferable.

A particularly preferable embodiment of a culture instrument will be described in detail as follows.

(Substrate of Culture Instrument)

A substrate that composes a culture instrument is not particularly limited, as long as the substrate is formed with a material so that an organic compound coating having a carbon-oxygen bond can be formed on the surface. Specific examples of such material include inorganic materials such as metal, glass, ceramic, and silicon and organic materials represented by elastomer and plastic (e.g., a polyester resin, a polyethylene resin, a polypropylene resin, an ABS resin, nylon, an acrylic resin, a fluorine resin, a polycarbonate resin, a polyurethane resin, a methylpentene resin, a phenol resin, a melamine resin, an epoxy resin, and a vinyl chloride resin). Shape of the substrate is also not limited and examples of the shape include planar shapes such as a flat plate, a flat membrane, a film, and a porous membrane and stereoscopic shapes such as a shape of Petri dish, a cylindrical shape, a shape of stamp, a shape of a multiwell plate, and a shape of a micro-flow path. When a culture instrument is in the form of a container such as Petri dish, culture can be performed using such culture instrument alone. When a culture instrument is not in the form of a container but in the form of flat plate, for example, such culture instrument may be used in combination with a general culture container. When there is a need to increase oxygen concentration upon cell culture or when there is a need to homogenize oxygen concentration distribution (concentration gradient) that is obtained by arranging cells (embedded in gel) between an solid substrate and an appropriate culture container as in the configuration of FIG.

3, a substrate with high oxygen permeability is preferably used. Examples of materials for forming such substrate include a silicone resin and silicone hydrogel that is used for high-oxygen-permeability soft contact lenses.
(Cell-Adhesion-Inhibiting Region)

A cell-adhesion-inhibiting region is preferably formed with a hydrophilic film that is formed with an organic compound having a carbon-oxygen bond. Such hydrophilic film is not particularly limited, as long as it is a thin film that is made of, as a main material, an organic compound having a carbon-oxygen bond and having water-solubility or water-swelling properties, has cell-adhesion-inhibiting properties before oxidation, and has cell adhesion properties after oxidation and/or degradation.

The term "carbon-oxygen bond" means a bond that is formed between carbon and oxygen and may not only be a single bond, but also be a double bond. Examples of such carbon-oxygen bond include a C-0 bond, a C(=O)-o bond, and a C=O bond.

Examples of such main raw material include water-soluble polymers, water-soluble oligomers, water-soluble organic compounds, surfactants, and amphiphiles. These materials physically or chemically cross-link each other to physically or chemically bind to a substrate, thereby forming a hydrophilic thin film.

Specific examples of such a water-soluble polymer material include polyalkyleneglycol and a derivative thereof, polyacrylic acid and a derivative thereof, polymethacrylic acid and a derivative thereof, polyacrylamide and a derivative thereof, polyvinyl alcohol and a derivative thereof, a zwitterionic polymer, and polysaccharides. Examples of the molecular shapes thereof include linear shapes, branched shapes, and dendrimers. More specific examples of such materials include, but are not limited to, polyethylene glycol, a copolymer of polyethylene glycol and polypropylene glycol (e.g., Pluronic F108, Pluronic F127, poly(N-isopropylacrylamide), poly(N-vinyl-2-pyrrolidone), poly(2-hydroxyethylmethacrylate), and poly(methacryloyloxyethylphosphorylcholine)), a copolymer of methacryloyloxyethylphosphorylcholine and acrylic monomer, dextran, and heparin.

Specific examples of water-soluble oligomer materials and water-soluble low-molecular-weight compounds include an alkylene glycol oligomer and a derivative thereof, an acrylate oligomer and a derivative thereof, a methacrylate oligomer and a derivative thereof, an acrylamide oligomer and a derivative thereof, a saponifiable substance of a vinyl acetate oligomer and a derivative thereof, an oligomer comprising zwitterionic monomers and a derivative thereof, acrylic acid and a derivative thereof, methacrylic acid and a derivative thereof, acrylamide and a derivative thereof, a zwitterionic compound, a water-soluble silane coupling agent, and a water-soluble thiol compound. More specific examples include, but are not limited thereto, an ethylene glycol oligomer, an (N-isopropylacrylamide) oligomer, a methacryloyloxyethylphosphorylcholine oligomer, a low-molecular-weight dextran, low-molecular-weight heparin, oligoethylene glycol thiol, ethylene glycol, diethylene glycol, triethylene glycol, tetraethylene glycol, 2-[methoxy(polyethyleneoxy)-propyltrimethoxysilane, and triethylene glycol-terminated-thiol.

A hydrophilic film has desirably high cell-adhesion-inhibiting properties before treatment but exhibits weak cell adhesion properties after oxidation treatment and/or degradation treatment.

The average thickness of such hydrophilic film preferably ranges from 0.8 nm to 500 µm, more preferably ranges from 0.8 nm to 100 µm, further more preferably ranges from 1 nm to 10 µm, and most preferably ranges from 1.5 nm to 1 µm. A hydrophilic film having an average thickness of 0.8 nm or more is preferred because such film is hardly affected by regions on the substrate surface not coated with the hydrophilic thin films upon protein adsorption or cell adhesion. With a hydrophilic film having an average thickness of 500 µm or less, coating can be relatively easily performed.

Examples of a method for forming a hydrophilic film onto a substrate surface include a method that involves causing direct adsorption of a hydrophilic organic compound to a substrate, a method that involves direct coating of a substrate with a hydrophilic organic compound, a method that involves coating a substrate with a hydrophilic organic compound and then performing cross-linking treatment, a method that involves forming a hydrophilic thin film in a multiple-step manner so as to enhance its adhesiveness to a substrate, a method that involves forming a foundation layer on a substrate so as to improve adhesiveness with the substrate and then coating the substrate with a hydrophilic organic compound, and a method that involves forming a polymerization initiation point on a substrate surface and then polymerizing hydrophilic polymer brush.

Examples of particularly preferable methods among the above film formation methods include a method that involves forming a hydrophilic thin film in a multiple-step manner and a method that involves forming a foundation layer on a substrate so as to improve adhesiveness with the substrate and then coating the substrate with a hydrophilic organic compound. This is because the use of these methods facilitates enhancement of the adhesiveness of a hydrophilic organic compound to a substrate. In this specification, the term "binding layer" is used. "Binding layer" means a layer that is present between a hydrophilic thin film layer on the outermost surface and a substrate when a hydrophilic organic compound thin film is formed in a multiple-step manner. When a foundation layer is provided on a substrate surface and a hydrophilic thin film layer is formed on the foundation layer, "binding layer" means the foundation layer. Such "binding layer" is preferably a layer containing a material having a binding portion (linker). Examples of a combination of a linker and a terminal functional group of a material to be bound to the linker include an epoxy group and a hydroxy group, a phthalic anhydride and a hydroxy group, a carboxyl group and an N-hydroxysuccinimide, a carboxyl group and carbodiimide, and an amino group and glutaraldehyde. Either one member of each of these combinations may serve as a linker. In these methods, a binding layer is formed with a material having a linker on a substrate before coating with a hydrophilic material. Density of the above material in a binding layer is an important factor for defining binding strength. Such density can be conveniently evaluated using the water contact angle of the surface of a binding layer as an indicator. For example, in the case of a silane coupling agent (epoxysilane) having an epoxy group at its end, if the water contact angle of the substrate surface to which epoxysilane is added is typically 45° or more and desirably 47° or more, a substrate having sufficient cell-adhesion-inhibiting properties can be prepared by subsequently adding an ethylene glycol material or the like in the presence of an acid catalyst.
(Formation of Cell Adhesion Region Via Oxidation Treatment and/or Degradation Treatment of Hydrophilic Film)

In a first embodiment, cell adhesion regions are each formed with a film prepared by subjecting a cell-adhesion-inhibiting hydrophilic film containing an organic compound having a carbon-oxygen bond to oxidation treatment and/or degradation treatment, so as to impart cell adhesion properties to the film. The thus formed cell adhesion regions have relatively weak cell adhesion ability, so that a pattern of cells or cell aggregates adhering onto the regions can be transferred rapidly to a material that interacts with cells relatively strongly like gel. Such cell adhesion regions have extremely weak cell adhesion, so that polarity of cells quickly changes when the configuration of FIG. 3 is employed, the cells adhere mainly to a gel layer, and then an environment similar to that in the case of three-dimensional culture can be easily generated. Moreover, even when the configuration of FIG. 3 is employed, a three-dimensional culture system as configured in FIG. 1 or a three-dimensional culture system as configured in FIG. 2 can be established within relatively a short time by peeling off a solid substrate (culture instrument) alone.

In the present invention, the term "oxidation" is a narrowly-defined term and means a reaction by which an organic compound reacts with oxygen so that the content of oxygen is increased compared with that before the reaction.

In the present invention, the term "degradation" indicates a change that is caused when bonds in the relevant organic compound are cleaved and then 2 or more types of organic compound are generated from 1 type of organic compound. Examples of "degradation treatment" include, but are not limited to, typically degradation by oxidation treatment and degradation due to ultraviolet irradiation. When "degradation treatment" means degradation accompanying oxidation (that is, oxidative degradation), "degradation treatment" and "oxidation treatment" indicate the same treatment.

Degradation due to ultraviolet irradiation indicates degradation that takes place when an organic compound adsorbs ultraviolet rays and then is degraded via its excited state. In addition, when a system in which an organic compound coexists with molecular species containing oxygen (e.g., oxygen and water) is irradiated with ultraviolet rays, in addition to degradation taking place after adsorption of ultraviolet rays by the compound, the molecular species may be activated to react with the organic compound. The latter reaction can be classified as "oxidation." Furthermore the reaction in which an organic compound is degraded by oxidation by activated molecular species can be classified not as "degradation due to ultraviolet irradiation," but by "degradation due to oxidation."

As described above, "oxidation treatment" and "degradation treatment" can overlap operationally and the two are not clearly distinguishable. In this specification, the term "oxidation treatment and/or degradation treatment" is used.

Examples of an oxidation treatment and/or degradation treatment method include a method that involves treating a hydrophilic film by ultraviolet irradiation, a method that involves treating the same by photocatalytic treatment, and a method that involves treating the same with an oxidizing agent. A hydrophilic film is partially subjected to oxidation treatment and/or degradation treatment depending on a desired cell pattern shape. When the film is partially subjected to oxidation treatment and/or degradation treatment, a mask such as a photomask or a stencil mask or a stamp is preferably used. Furthermore, oxidation treatment and/or degradation treatment may be performed by a direct drawing method such as a method using laser such as ultraviolet laser.

When ultraviolet irradiation treatment is performed, a lamp that is preferably used as a light source generates ultraviolet rays between the VUV range and the UV-C range. Examples of such lamp include a mercury lamp generating ultraviolet rays with a wavelength of 185 nm or 254 nm and an excimer lamp generating ultraviolet rays with a wavelength of 172 nm. When photocatalytic treatment is performed, a light source that is preferably used herein generates ultraviolet rays with a wavelength of 365 nm or less and the same that is more preferably used generates ultraviolet rays with a wavelength of 254 nm or less. As a photocatalyst, a titanium oxide photocatalyst or a titanium oxide photocatalyst that is activated using a metal ion or a metal colloid is preferably used. As an oxidizing agent, organic acid or inorganic acid can be used without particular limitation. However, since handling of high-concentration acid is difficult, such acid is preferably diluted at a concentration of 10% or less and then used. Optimum time for treatment with ultraviolet rays, optimum time for photocatalytic treatment, and optimum time for treatment with an oxidizing agent can be adequately determined according to various conditions including intensity of ultraviolet rays that are generated from a light source to be used, photocatalyst activity, oxidizing power of an oxidizing agent, concentration of an oxidizing agent, and the like.

(Formation of Cell Adhesion Region Via Achievement of Lower Density of Hydrophilic Film)

In a second embodiment, cell adhesion regions are formed with a hydrophilic film containing a low-density organic compound having a carbon-oxygen bond. The thus formed cell adhesion regions also have relatively weak cell adhesion ability, so that a pattern of cells or cell aggregates adhering onto the regions can be transferred rapidly to a material that interacts with cells relatively strongly like gel. Such cell adhesion regions have extremely weak cell adhesion, so that polarity of cells quickly changes when the configuration of FIG. 3 is employed, the cells adhere mainly to a gel layer, and then an environment similar to that in the case of three-dimensional culture can be easily generated. Moreover, even when the configuration of FIG. 3 is employed, a three-dimensional culture system as configured in FIG. 1 or a three-dimensional culture system as configured in FIG. 2 can be established within relatively a short time by peeling off a solid substrate (culture instrument) alone.

In this embodiment, both cell adhesion regions and cell-adhesion-inhibiting regions are each formed with a hydrophilic film containing an organic compound having a carbon-oxygen bond. The two regions differ in terms of the density of the organic compound. There is a tendency that the higher the density, the more hardly the cells adhere. In the case of the cell adhesion regions, the density of the organic compound is at a low level such that cells can adhere. On the other hand, in the case of the cell-adhesion-inhibiting regions, the density of the organic compound is at a high level such that cells cannot adhere.

An example of a method for controlling the density of such a hydrophilic organic compound is a method that involves providing a binding layer between a hydrophilic organic compound thin film and a substrate surface and adjusting strength for binding of the binding layer with the hydrophilic organic compound. Here "binding layer" is as defined above and can be composed of preferable materials that are explained above. Regarding the binding strength of a binding layer, the higher the density of a material having a linker in the binding layer, the stronger the binding strength; and the lower the density of the same, the weaker the binding strength. Density of a material having a linker in a binding layer can be conveniently evaluated using the water contact angle of the surface of a binding layer as an indicator, as described above.

In this embodiment, the density of a material having a linker of a binding layer in cell adhesion regions is low. For example, the water contact angle of the surface of a binding layer before formation of a hydrophilic organic compound thin film in cell adhesion regions typically ranges from 10° to 43° and desirably ranges from 15° to 40° when a silane coupling agent (epoxysilane) having an epoxy group at its end as a material having a linker is used. An example of a method for forming such a binding layer is a method that involves forming a coat (binding layer) made of a material having a linker on a substrate surface and then subjecting the binding layer surface to oxidation treatment and/or degradation treatment. Examples of a method for subjecting such a binding layer surface to oxidation treatment and/or degradation treatment include a method that involves subjecting a binding layer surface to ultraviolet irradiation, a method that involves performing photocatalytic treatment, and a method that involves performing treatment with an oxidizing agent. A binding layer surface may be partially subjected to oxidation treatment and/or degradation treatment depending on the shape of a desired cell pattern. Partial treatment can be performed using a mask such as a photomask or a stencil mask or a stamp. Furthermore, oxidation treatment and/or degradation treatment may also be performed by a direct drawing method such as a method using laser such as ultraviolet laser. Regarding various conditions applicable herein, conditions similar to those for a method for forming cell adhesion regions through oxidation treatment and/or degradation treatment performed for a hydrophilic film can be employed herein. Cell adhesion regions can be formed by forming a hydrophilic organic compound thin film on the thus formed binding layer.

In this embodiment of the present invention, the density of a material having a linker of a binding layer in cell-adhesion-inhibiting regions is high. For example, the water contact angle of the surface of a binding layer before formation of a hydrophilic organic compound thin film in cell-adhesion-inhibiting regions is typically 45° or more and desirably 47° or more when a silane coupling agent (epoxysilane) having an epoxy group at its end as a material having a linker is used. Such a binding layer can be obtained by forming a coat made of a material having a linker on a substrate surface. When a binding layer surface is partially subjected to oxidation treatment and/or degradation treatment, the remaining untreated portion is a binding layer having the above-mentioned water contact angle. Cell-adhesion-inhibiting regions can be formed by forming a hydrophilic organic compound thin film on the thus formed binding layer.

(Comparison of Cell Adhesion Region with Cell-Adhesion-Inhibiting Region)

The following explanation is applicable to both embodiments described above.

A difference in height between a cell adhesion region (and when a binding layer is present, the binding layer is also included) and a cell-adhesion-inhibiting region (and when a binding layer is present, the binding layer is also included) is preferably 10 nm or less. This is because such difference in height prevents inhibition of cell movement in a planar direction in the case of a three-dimensional culture with the configuration of FIG. 3. Either cell adhesion regions or cell-adhesion-inhibiting regions can be convex.

Carbon content in cell adhesion regions (when a binding layer is present, the binding layer is also included) is preferably lower than that in cell-adhesion-inhibiting regions (when a binding layer is present, the binding layer is also included). Specifically, carbon content in cell adhesion regions preferably ranges from 20% to 99% with respect to that in cell-adhesion-inhibiting regions. Such carbon content within the range is particularly preferable when hydrophilic film thickness (the sum of binding layer thickness and hydrophilic film thickness when a binding layer is present) is 10 µm or less. "Carbon content (atomic concentration %)" is as defined below.

Moreover, the proportion of carbon (%) binding to oxygen among all the carbon members in cell adhesion regions (when a binding layer is present, the binding layer is also included) is preferably lower than the proportion of carbon (%) binding to oxygen among all the carbon members in cell-adhesion-inhibiting regions (when a binding layer is present, the binding layer is also included). Specifically, the proportion of carbon (%) binding to oxygen among all the carbon members in cell adhesion regions is preferably 35% to 99% with respect to the proportion of carbon (%) binding to oxygen among all the carbon members in cell-adhesion-inhibiting regions. Such carbon content within this range is particularly preferable when hydrophilic film thickness (the sum of binding layer thickness and hydrophilic film thickness when a binding layer is present) is 10 µm or less. "Proportion of carbon binding to oxygen (atomic concentration %)" is as defined below.

(Method for Evaluating Hydrophilic Thin Film)

Examples of a technique that can be used for evaluating the hydrophilic thin film (when a binding layer is present, the binding layer is also included) of the present invention include contact angle measurement, Ellipsometry, observation under an atomic force microscope, observation under an electron microscope, measurement by Auger electron spectroscopy, measurement by X-ray photoelectron spectroscopy, various types of mass spectroscopy, measurement using a white-light interferometer, observation under a confocal laser microscope, and observation under a probe-type laser microscope. Among these techniques, X-ray photoelectron spectroscopy (XPS/ESCA) has the most excellent quantitative capability. Relative quantitative values can be found by this measurement technique and are generally calculated based on element concentrations (atomic concentrations %). X-ray photoelectron spectroscopy in the present invention is described in detail as follows.

(Method for Calculating Carbon Content in Hydrophilic Thin Film and Method for Calculating the Proportion of Carbon Binding to Oxygen)

In the present invention, "carbon content" in a hydrophilic thin film is defined as "carbon content that can be found from the analytical value of C1s peak obtained using an X-ray photoelectron spectroscopy apparatus." Furthermore, in the present invention, "proportion of carbon binding to oxygen" in a hydrophilic thin film is defined as "proportion of carbon binding to oxygen, which is found from the analytical value of C1s peak obtained using an X-ray photoelectron spectroscopy apparatus." Two specific measurement methods are as described below. In addition, measurement methods in the present invention are not limited to these measurement methods.

(Measurement Method 1)

X-ray photoelectron spectroscopy apparatus: VG_Theta Probe produced by Thermo Environmental Instruments Inc.
X-ray source: Monochromated aluminium Kα ray (15 kV-6.67 mA=100 W).
Measurement area: 400 µmφ
Positional relationship between a sample and a detector: A lens for taking photoelectrons is set at a position having an angle of 53° with respect to the normal line of the sample
Carbon content: A photoelectron set to be measured is determined through assumption of elements composing a substrate or a hydrophilic thin film. The concentration of an element (atomic concentration) derived from each photoelectron is calculated based on the measured total photoelectron yield that is determined to be 100%. Element concentration (atomic concentration %) of C1s peak is determined to be a carbon content.
Method for C1s peak fitting: Fitting is performed for C—O bond, C(=O)—O bond, C=O bond, and C—C bond.
Formula for calculating the proportion of carbon binding to oxygen: {[proportion of carbon in C—O bond]+[proportion of carbon in C(=O)—O bond]+[proportion of carbon in C=O bond]}÷{[proportion of carbon in C—O bond]+[proportion of carbon in C(=O)—O bond]+[proportion of carbon in C=O bond]+[proportion of carbon in C—C bond]+[(if necessary) proportion of carbon in the other bonds]}×100 (%).

In addition, if necessary, fitting is also performed for the other bonds. Based on the resulting data, concentration of carbon (atomic concentration %) in each binding condition of C1s peak is calculated.

(Measurement Method 2)

X-ray photoelectron spectroscopy apparatus: ESCA-3400 (Amicus) produced by KRATOS Analytical.

X-ray source: Non-monochromated magnesium Kα ray (10 kV-20 mA=200 W).

Measurement area: 6 mmφ

Positional relationship between a sample and a detector: A lens for taking photoelectrons is set on the normal line of the sample Carbon content: A photoelectron set to be measured is determined through assumption of elements composing a substrate or a hydrophilic thin film. The concentration of an element (atomic concentration) derived from each photoelectron is calculated based on the measured total photoelectron yield that is determined to be 100%. Element concentration (atomic concentration %) of C1s peak is determined to be a carbon content.

Method for C1s peak fitting: Fitting is performed for C—O bond, C(=O)—O bond, C=O bond, and C—C bond.

Formula for calculating the proportion of carbon binding to oxygen: {[proportion of carbon in C—O bond]+[proportion of carbon in C(=O)—O bond]+[proportion of carbon in C=O bond]}÷{[proportion of carbon in C—O bond]+[proportion of carbon in C(=O)—O bond]+[proportion of carbon in C=O bond]+[proportion of carbon in C—C bond]+[(if necessary) proportion of carbon in the other bonds]}×100 (%).

In addition, if necessary, fitting is also performed for the other bonds. Based on the resulting data, concentration of carbon (atomic concentration %) in each binding condition of C1s peak is calculated.

(Biological Test Method)

The biological test method of the present invention is to test a biological indicator relating to at least one selected from the group consisting of proliferation, movement, and differentiation of cells in a cell pattern that is prepared by the above procedures so that the cell pattern is substantially embedded in gel.

Specifically, a biological indicator tested herein relates to at least one selected from the group consisting of proliferation, movement, and differentiation of cells under conditions where gel or medium existing around a cell pattern contains a drug or cells depending on the purpose of a test. As shown in FIG. 4, a plurality of cells can also be tested simultaneously in terms of biological indicators with the use of a combination of a plurality of cell patterns. Furthermore, as shown in FIG. 5, cell complexes can be tested in terms of biological indicators by causing a plurality of cell patterns to come into contact with each other. During such a test, cell patterns and gel are preferably maintained under temperature conditions where cells can undergo proliferation, movement, or differentiation. Gel or medium contains a solvent, a buffer, and the like that are appropriate for cell proliferation, movement, or differentiation if necessary.

Examples of such "a biological indicator relating to at least one selected from the group consisting of cell proliferation, movement, and differentiation" include total amount of genes, cell cycle, number of cells, ratio of viable cells to dead cells, distance that each cell moves during an arbitrary time length, direction toward which each cell moves, variations in cell-to-cell binding, such as tight junction, adherence junction, and gap junction, and enhancement or suppression of the expression of various differentiation markers depending on cell types or differentiation conditions.

According to the present invention, various tests can be performed based on such biological indicators. Examples of such tests include, but are not particularly limited thereto, a cytotoxicity test, a chemical migration test, a test of a protein phosphorylation inhibitor, a test of a G protein signal second messenger inhibitor, a test of a calmodulin phosphorylation protein inhibitor, a test of a cyclin-dependent protein phosphorylation inhibitor, a test of a MAP phosphorylation-related inhibitor, a test of a tyrosine phosphorylation inhibitor, a test of a Wnt signal-related inhibitor, a test of an Akt phosphorylation signal inhibitor, a test of a Notch signal inhibitor, a test of a protein dephosphorylation inhibitor, a test of a cytokine signaling inhibitor, a test of a hormone inhibitor, a test of an HDAC inhibitor, a test of an NFκB inhibitor, a test of an agent inhibiting the nucleus-to-cytoplasm transport of substances, a test of a nervous system-related inhibitor (e.g., calcium signal), a test of a proteinase inhibitor, a test of an agent inhibiting an enzyme that degrades an extracellular matrix, a test of an inhibitor relating to oxidative stress, a test of an apoptosis inducer or inhibitor, a test of a vascularization inducer or inhibitor, a test of a cytoskeleton inhibitor, a test of a cell division inhibitor, a test of a telomerase inhibitor, a test of a saccharification inhibitor, a test of DNA synthesis inhibitor, and a test of a drug (e.g., antitumor drugs).

A method for culturing cells, which is performed in the biological test method of the present invention, is not particularly limited. For example, general closed culture using dishes, multiwell plates, or the like or perfusion culture using bioreactors or the like is employed.

(Observation of Cell Movement)

For observation of cell movement, it is preferable to take moving pictures of cell movement followed by analysis of moving pictures, for example.

(Method for Taking Moving Pictures)

A typical example of a method for taking moving pictures is as described below. A photographic device that enables observation and recording under a microscope at a temperature of 37° C. and with $CO_2$ concentration of 5% is used. Appropriate time intervals for taking moving pictures differ depending on cells and may be any time intervals as long as the direction of cell movement does not change significantly. For example, an appropriate time interval ranges from approximately 1 to 5 minutes for the movement of bovine vascular endothelial cells on glass.

(Method for Analyzing Moving Pictures)

With the use of moving pictures recorded, the cell center of gravity or the cell nucleus is determined to be the position of the cell and the time variations of the relevant position coordinate are recorded for each cell. Examples of quantifiable parameters include velocity vectors or the population mean thereof, spatiotemporal correlation functions for velocity, mean-square displacement or a parameter representing its time dependency, and area enclosing cell populations. Furthermore, when cell orientation can be specified such that cells are elliptically shaped, a spatiotemporal correlation function for orientation can also be quantified as a parameter. A velocity vector can be obtained by dividing a displacement vector (obtained when cells migrate at each time interval) by the time (required for the migration). When the velocity vectors of a cell population are averaged, how the whole cell population moves can be revealed. A spatiotemporal correlation function for velocity is obtained as the mean cosine of an angle between velocity vectors. A temporal correlation function is obtained via time averaging in terms of specific cells; and a spatial correlation function is obtained via averaging in terms of the certain cell-to-cell distance using a fixed time length. A spatiotemporal correlation function is a value ranging from 0 to 1. The larger the value of a spatiotemporal correlation function, the stronger the correlation between velocity vectors and the more uniform movement direction. Mean-square displacement is obtained by averaging the squared values obtained for a cell population, each of which is the squared value of the cell migration distance that cells migrate after a time length (from a time point determined to be an initial value). Such mean-square displacement provides information about how the cell population diffuses. If time dependency of mean-square displacement is supposed to be a value obtained by raising the time to the power of $\alpha$, parameter $\alpha$ can be obtained by fitting. When each cell moves randomly, $\alpha$ is 1. "$\alpha$" closer to 2 means ballistic cell movement. Area S enclosing a cell population corresponds to the average value of the squared values each of which is the squared value of the distance between the cell population center of gravity and each cell. A spatiotemporal correlation function for cell orientation is obtained by the same calculation method that is employed for a spatiotemporal correlation function for velocity. Specifically, a directional vector representing cell orientation is replaced by a velocity vector. The larger the value of a correlation function, the higher the orientation. It is convenient to use appropriate image analysis software for analysis. Examples of free image analysis software include imageJ (http://rsb.info.nih.gov/ij) and scion image (http://www.scioncorp.com).

(Biological Test Kit)

The present invention further provides a biological test kit containing the above-mentioned culture instrument and gel. The kit of the present invention may also contain a buffer for cell culture, a container (e.g., multiwell plate) for cell culture, a drug for a test, an instruction manual, and the like, if necessary. Gel in such kit may also be in the form of solid substances (including powders) that can be gelled by the addition of a solvent such as water or a buffer when used.

An example of the use of this kit is as follows. Necessary materials such as commercial multiwell plates, gel, and test substances are prepared. Some types of cells of specific organs derived from mammals of different species are pattern-cultured using the above-mentioned culture instruments. These cells of mammalian species are cultured species by species. The three-dimensional culture test of the present invention is performed at the same time in different wells of the multiwell plate, so that differences in terms of action among different species are tested.

EXAMPLES

Example 1

Preparation of Substrate for Cell Culture (First-Step Reaction)

39.0 g of toluene and 2.25 g of TSL8350 (produced by GE Toshiba Silicone) were mixed. 450 µl of triethylamine was added to the solution while stirring. After several minutes of stirring of the solution at room temperature, the total volume of the solution was transferred to a glass plate. A 10-cm square glass substrate that had been washed with UV was immersed in the solution and then the substrate was allowed to stand at room temperature for 16 hours. Subsequently, the glass substrate was washed with ethanol and water and then dried by nitrogen blowing. The water contact angle of the substrate surface was approximately 53°.

(Second-Step Reaction)

25 µl of concentrated sulfuric acid was added dropwise to 50 g of tetraethylene glycol (TEG) while stirring. After several minutes of stirring of the solution, the total volume of the solution was transferred to a glass plate. The above substrate was immersed in the solution, followed by 20 minutes of reaction at 80° C. After reaction, the substrate was washed well with water and then dried by nitrogen blowing. As a result, an organic thin film containing TEG was formed on the glass substrate surface. The water contact angle of the surface was approximately 28°.

(Oxidation Treatment)

A photomask coated with a titanium oxide photocatalyst was prepared. The photomask used herein comprises a linear pattern (wherein openings each having a width of 60 µm are provided at a pitch of 300 µm) and linear openings each having a width of 60 µm and orthogonally crossing the aforementioned linear pattern at intervals of 2.5 cm. The photocatalyst layer of the photomask was caused to come into contact with the above film formation face and then installed in an exposure apparatus, so that ultraviolet irradiation was performed from the photomask side. Light exposure was performed for 35 seconds using a mercury lamp having illuminance of 20 mW/cm$^2$ at a wavelength of 365 nm, so that the hydrophilic thin film on the substrate surface was partially subjected to oxidative degradation. This substrate was cut into a size of 25 mm×15 mm and then the resultant was used as a cell adhesion substrate.

(Cell Culture)

An autoclave-sterilized substrate was arranged within a culture container and then an appropriate amount of MEM medium containing 5% fetal calf serum was added. 2.0×10$^5$ bovine aortic vascular endothelial cells were seeded per substrate. After 48 hours of culture within an incubator (37° C., 5% $CO_2$), cells adhered only to oxidatively degraded regions and reached confluency on the lines each having a width of 60 µm.

(Cell Transfer and Three-Dimensional Culture with the Configuration of FIG. 2)

A collagen solution was prepared on ice using a collagen gel culture kit (Cellmatrix I-A, Nitta gelatin). 500 µl of the solution was spread flatly over a 28 mm×33 mm well, followed by 10 minutes of gelling at 37° C. 2 ml of MEM medium containing 5% fetal calf serum was added to the gel. The substrate was caused to sink while upside-down in the medium, so that cells that had adhered to the substrate were caused to come into contact with collagen gel at the bottom. After 4 hours of culture within an incubator, the substrate was carefully removed using a pair of tweezers. Almost all the cells had tube-like structures in the collagen gel. The medium was removed by suction, 250 µl of the collagen solution was applied in layers to the cells, and then gelling was performed at 37° C. for 10 minutes. Subsequently, 2 ml of MEM medium containing 5% fetal calf serum, to which proliferation factors (a 10 ng/ml vascular endothelial cell proliferation factor, a 10 ng/ml basic fibroblast proliferation factor, and 50 µg/ml heparin) had been added, was added. The three-dimensional culture with the configuration of FIG. 2 was then performed. After 24 hours of culture, the phenomenon of new vessels growing from the existing tube-like structures was observed. This is a phenomenon referred to as vascularization, in which proliferation and migration take place while maintaining cell-to-cell adhesion. This is also a representative example of collective cell migration. Thereafter, vascularization consecutively took place. At one week after culture, extremely branched capillary-like networks had formed at high density. In contrast, when suramin (50 μM), a type of vascularization inhibitor, was added to the three-dimensional culture system, the vascularization thereof was completely inhibited.

Example 2

(First-Step Reaction)

39.0 g of toluene and 1.20 g of TSL8350 (produced by GE Toshiba Silicone) were mixed. 450 μl of triethylamine was added to the solution while stirring. After several minutes of stirring of the solution at room temperature, the total volume of the solution was transferred to a glass plate. A 10-cm square glass substrate that had been washed with UV was immersed in the solution and then the substrate was allowed to stand at room temperature for 16 hours. Subsequently, the glass substrate was washed with ethanol and water and then dried by nitrogen blowing. The water contact angle of the substrate surface was approximately 51°.

(Second-Step Reaction)

25 μl of concentrated sulfuric acid was added dropwise to 50 g of tetraethylene glycol (TEG) while stirring. After several minutes of stirring of the solution, the total volume of the solution was transferred to a glass plate. The above substrate was immersed in the solution, followed by 20 minutes of reaction at 80° C. After reaction, the substrate was washed well with water and then dried by nitrogen blowing. As a result, an organic thin film containing TEG was formed on the glass substrate surface. The water contact angle of the surface was approximately 28°.

(Oxidation Treatment)

A photomask coated with a titanium oxide photocatalyst was prepared. The photomask used herein comprises a linear pattern (wherein openings each having a width of 60 μm are provided at a pitch of 300 μm) and linear openings each having a width of 60 μm and orthogonally crossing the aforementioned linear pattern at intervals of 2.5 cm. The photocatalyst layer of the photomask was caused to come into contact with the above film formation face and then installed in an exposure apparatus, so that ultraviolet irradiation was performed from the photomask side. Light exposure was performed for 35 seconds using a mercury lamp having illuminance of 20 mW/cm$^2$ at a wavelength of 365 nm, so that the hydrophilic thin film on the substrate surface was partially subjected to oxidative degradation. This substrate was cut into a size of 25 mm×15 mm and then the resultant was used as a cell adhesion substrate.

(Cell Culture)

An autoclave-sterilized substrate was arranged within a culture container and then an appropriate amount of MEM medium containing 5% fetal calf serum was added. 2.0×10$^5$ bovine aortic vascular endothelial cells were seeded per substrate. After 72 hours of culture, cells adhered only to oxidatively degraded regions and reached confluency on the lines each having a width of 60 μm.

(Cell Transfer and Three-Dimensional Culture with the Configuration of FIG. 3)

200 μl of ice-cooled Growth Factor Reduced (GFR) Matrigel (Becton, Dickinson and Company) was spread over a culture container and then allowed to stand at room temperature for approximately 1 minute. The substrate was gently placed with its cell adhesion face down onto the matrigel. The resultant was allowed to stand for approximately 5 minutes while maintaining this condition. After complete gelling, MEM medium containing 5% fetal calf serum was added and then the substrate was immersed in the medium. The culture container was transferred into an incubator (37° C., 5% CO$_2$) and then cells were cultured while being sandwiched between a substrate and matrigel. 3 hours later, cell populations that had adhered onto the substrate significantly shrinked to form cylindrical masses. This is a phenomenon that is characteristically observed when vascular endothelial cells undergo lumen formation in response to differentiation signals coming from the extracellular matrix. When a vascularization inhibitor had been previously added to the three-dimensional culture system, shrinkage of multiple cells was inhibited or not inhibited according to the relevant pharmacologic action (Table 1). This means that the effect of a drug on lumen formation can be efficiently tested via observation of cell shrinkage that is observed at the initial stage of differentiation. This test method could also be performed for normal human umbilical vein endothelial cells in completely the same manner.

TABLE 1

Various drugs' effects of inhibiting lumen formation in the test method

| Inhibitor | Action mechanism | Inhibition effect |
|---|---|---|
| Suramin | Inhibition of the binding of a proliferation factor with its receptor | x |
| BT | Inhibition of cell proliferation and MMP activity | Δ |
| Amiloride | Inhibition of u-PA activity | x |
| Minocycline | Inhibition of MMP3 activity | x |
| Anti-VE-cadherin antibody | Inhibition of cell-to-cell adhesion | x |
| RGD peptide | Inhibition of binding with fibronectin | x |
| YIGSR-NH$_2$ peptide | Inhibition of binding with laminin | Δ |
| PP2 | Inhibition of tyrosine kinase Src activity | ○ |
| LY294002 | Inhibition of PI3 kinase activity | Δ |
| Akt inhibitor | Inhibition of Akt kinase activity | x |
| Y27632 | Inhibition of Rho kinase activity | x |

○ . . . Large inhibition effect,
Δ . . . Small inhibition effect, and
x . . . No inhibition effect Example 3

(First-Step Reaction)

39.0 g of toluene and 0.56 g of TSL8350 (produced by GE Toshiba Silicone) were mixed. 450 μl of triethylamine was added to the solution while stirring. After several minutes of stirring of the solution at room temperature, the total volume of the solution was transferred to a glass plate. A 10-cm square glass substrate that had been washed with UV was immersed in the solution and then the substrate was allowed to stand at room temperature for 16 hours. Subsequently, the glass substrate was washed with ethanol and water and then dried by nitrogen blowing. The water contact angle of the substrate surface was approximately 50°.

(Second-Step Reaction)

25 μl of concentrated sulfuric acid was added dropwise to 50 g of TEG while stirring. After several minutes of stirring of the solution, the total volume of the solution was transferred to a glass plate. The above substrate was immersed in the solution, followed by 2 hours of reaction at 80° C. After reaction, the substrate was washed well with water and then dried by nitrogen blowing. As a result, an organic thin film containing TEG was formed on the glass substrate surface. The water contact angle of the substrate surface was approximately 27°.

(Oxidation Treatment)

A photomask coated with a titanium oxide photocatalyst was prepared. The photomask used herein comprises a linear pattern (wherein openings each having a width of 60 μm are provided at a pitch of 300 μm) and linear openings each having a width of 60 μm and orthogonally crossing the aforementioned linear pattern at intervals of 2.5 cm. The photocatalyst layer of the photomask was caused to come into contact with the above film formation face and then installed in an exposure apparatus, so that ultraviolet irradiation was performed from the photomask side. Light exposure was performed for 35 seconds using a mercury lamp having illuminance of 20 mW/cm$^2$ at a wavelength of 365 nm, so that the hydrophilic thin film on the substrate surface was partially subjected to oxidative degradation. This substrate was cut into a size of 25 mm×15 mm and then the resultant was used as a cell adhesion substrate.

(Cell Culture)

An autoclave-sterilized substrate was arranged within a culture container and then an appropriate amount of MEM medium containing 5% fetal calf serum was added. $2.0 \times 10^5$ bovine aortic vascular endothelial cells were seeded per substrate. After 72 hours of culture, cells adhered only to oxidatively degraded regions and reached confluency on the lines each having a width of 60 μm.

(Cell Transfer and Three-Dimensional Culture with the Configuration of FIG. 3)

200 μl of ice-cooled Growth Factor Reduced (GFR) Matrigel (Becton, Dickinson and Company) was spread over a culture container and then allowed to stand at room temperature for approximately 1 minute. The substrate was gently placed with its cell adhesion face down onto the matrigel. The resultant was allowed to stand for approximately 5 minutes for gelling while maintaining this condition. MEM medium containing 5% fetal calf serum was added and then the substrate was immersed in the medium. The culture container was transferred into an incubator (37° C., 5% $CO_2$) and then cells were cultured while being sandwiched between a substrate and matrigel. 3 hours later, cell populations that had adhered onto the substrate significantly shrunk to form cylindrical masses when they were observed under a phase-contrast microscope. Based on the extremely unclear interface between cells at this time, it was concluded that cell-to-cell adhesion had been highly developed via lamination of matrigel. However, when culture was continued under the same conditions, cell populations at the initial stage of differentiation underwent dedifferentiation within 24 hours and disintegration of cell-to-cell adhesion and single cell migration were observed. This three-dimensional culture system was thought to be a culture system useful for testing switching between differentiation and dedifferentiation of vascular endothelial cells and for testing the development and disintegration of cell-to-cell adhesion.

Example 4

Preparation of Substrate for Cell Culture (First-Step Reaction)

A solution was prepared by mixing 39 g of toluene, 13.5 g of epoxysilane (TSL8350, GE Toshiba Silicone), and 450 μl of triethylamine. A predetermined amount of the thus prepared solution was transferred into a glass Petri dish. A 10-cm square glass plate having a thickness of 0.7 mm, which had been washed with UV, was immersed in the solution and then the plate was allowed to stand at room temperature for 16 hours for reaction. Subsequently, the glass plate was washed with ethanol, subjected to ultrasonic washing with water, and then dried. The water contact angle of the glass plate surface was approximately 50.1°.

(Second-Step Reaction)

25 μl of concentrated sulfuric acid was added to 50 g of tetraethylene glycol while stirring. A predetermined amount of the solution was transferred to a glass Petri dish. The above epoxidized glass plate was immersed in the solution, followed by 20 minutes of reaction at 80° C. After reaction, the substrate was washed with water and then dried. The surface water contact angle was measured and the water contact angle was 29.4° on an average.

(Oxidation Treatment)

A photomask coated with a titanium oxide photocatalyst was prepared. The photomask used herein comprises a linear pattern (wherein openings each having a width of 60 μm are provided at a pitch of 300 μm), linear openings each having a width of 60 μm and orthogonally crossing the aforementioned linear pattern at intervals of 2.5 cm, and openings each having a width of approximately 1.5 cm provided in the periphery of the photomask. The illuminance of an exposure apparatus was measured in advance at a wavelength of 350 nm and the measured value was used as an indicator for determination of time of exposure. The illuminance was 18.6 mW/cm$^2$. The glass substrate on which a hydrophilic thin film had been formed and the photomask were arranged so that the hydrophilic thin film faced the catalyst layer of the photomask and they were installed in the exposure apparatus so that light came from the photomask side. Light exposure was performed for 57 seconds, so that oxidative degradation was performed. This substrate was then cut into a size of 24 mm×15 mm to facilitate the use of the substrate for culture.

(Cell Culture)

Each of the above cut substrate was subjected to high pressure vapor sterilization using an autoclave. The substrate was arranged within a culture container. $1.5 \times 10^5$ vascular endothelial cells (BAEC: bovine aortic endothelial cells) of bovine carotid artery were seeded per substrate. MEM medium containing 5% serum was used and then cells were cultured for 48 hours within an incubator at 37° C. and with 5% $CO_2$ concentration. When observed under a fluorescence phase-contrast microscope, BAECs adhered only to portions subjected to oxidation treatment.

(Cell Transfer and Three-Dimensional Culture)

200 μl of matrigel (trademark) was spread over a culture container and then allowed to stand at room temperature for several minutes so that gelling was performed to some extent. $5 \times 10^5$ cells/mL mouse-derived fibroblasts that had been fluorescence-labeled with PKH26 in advance were injected into the matrigel (trademark). The cell culture substrate was placed so as to face the matrigel (trademark). Subsequently, D-MEM medium containing 10% serum was added, followed by 3 hours of culture at 37° C. and 5% $CO_2$ within an incubator. At this time point, it was confirmed under a fluorescence phase-contrast microscope that BAECs had undergone a morphological change so as to form a tube shape. It was also confirmed under a fluorescence phase-contrast microscope that almost no fibroblasts had migrated within the matrigel. The substrate was carefully peeled off using a pair of tweezers. BAECs were transferred onto the matrigel (trademark) and then cultured for 2 hours at 37° C. and 5% $CO_2$ within an incubator. At this time point, it was confirmed under a fluorescence phase-contrast microscope that almost no BAECs and almost no fibroblasts had migrated.

Example 5

Preparation of Substrate for Cell Culture (First-Step Reaction)

A solution was prepared by mixing 39 g of toluene, 0.7 g of epoxysilane (TSL8350, GE Toshiba Silicone), and 400 µl of triethylamine. A predetermined amount of the thus prepared solution was transferred into a container. A 10-cm square glass plate having a thickness of 0.7 mm, which had been washed with ultraviolet rays, was immersed in the solution. After 18 hours of reaction at room temperature, the glass plate was washed with toluene, washed with ethanol, and then finally subjected to ultrasonic washing with water. The water contact angle of the glass plate surface was 51.3° on an average.

(Second-Step Reaction)

25 µl of concentrated sulfuric acid was added to 50 g of tetraethylene glycol while stirring. A predetermined amount of the solution was transferred to a container. The above epoxidized glass plate was immersed in the solution, followed by 20 minutes of reaction at 80° C. After reaction, the substrate was washed well with water. The water contact angle of the glass plate surface was 32.0° on an average. Thus, the glass plate on which a hydrophilic thin film had been formed could be prepared.

(Oxidation Treatment)

A photomask coated with a titanium oxide photocatalyst was prepared. The photomask used herein comprises 100 µm-square opening array regions formed at a pitch of 200 µm, 200 µm-square opening array regions formed at a pitch of 400 µm, 300 µm-square opening array regions formed at a pitch of 600 µm, 400 µm-square opening array regions formed at a pitch of 800 µm, and openings each having a width of approximately 1.5 cm formed in the periphery of the photomask. The illuminance of an exposure apparatus was measured in advance at a wavelength of 350 nm and the measured value was used as an indicator for determination of time of exposure. The illuminance was 18.6 mW/cm$^2$. The glass plate on which a hydrophilic thin film had been formed and the photomask were arranged so that the hydrophilic thin film faced the photocatalyst layer of the photomask and they were installed in the exposure apparatus so that irradiation with ultraviolet rays was performed from the back side of a quartz plate. Light exposure was performed for 161 seconds, so that oxidative treatment was performed. Subsequently, this substrate was cut into a size of 24 mm×15 mm for use in culture. Portions facing the openings in the periphery of the photomask were used for X-ray Photoelectron Spectroscopy (XPS).

(Surface Analysis)

Hydrophilic thin films were measured before and after oxidation treatment using a VG_Theta Probe produced by Thermo Environmental Instruments Inc. C1s peak fitting was performed for carbons of C—C bonds, carbons of C—O bonds, carbons of C(=O)—O bonds and C=O bonds. The thus obtained carbon content of the hydrophilic thin film measured after oxidation treatment was 85.3% of the carbon content of the hydrophilic thin film measured before oxidation treatment. Furthermore, the proportion of carbon binding to oxygen in the hydrophilic thin film measured before oxidation treatment was 76.7%; and the proportion of carbon binding to oxygen in the hydrophilic thin film measured after oxidation treatment was 64.6%. Furthermore, the water contact angle of the hydrophilic thin film surface measured after oxidation treatment was 28.8°. Furthermore, the patterning surface was observed using a scanning white-light interferometer (Zygo NewView 5000). An approximately 1-nm difference in height was formed depending on the mask pattern.

(Cell Culture)

Each of the above cut substrate for pattern culture (on which 200 µm-square cell adhesion regions had been formed at a pitch of 400 µm) was subjected to high pressure vapor sterilization using an autoclave. The substrate was arranged within a culture container. 2×10$^5$ normal human (adult) dermal fibroblasts (KF-4109, Cascade Biologics) dispersed in a culture solution (basal medium M-106-5005, additive agent KE-6350, Cascade Biologics/KURABO) were seeded per substrate. Fibroblasts were cultured for 46 hours under conditions of 37° C. and 5% $CO_2$ using an incubator. Cell patch arrays comprising monolayered fibroblasts were formed. Whereas fibroblasts in the patch central portions became relatively smaller in size, fibroblasts in the patch peripheral portions were relatively spindle-shaped.

(Cell Transfer and Three-Dimensional Culture with the Configuration of FIG. 2)

A reagent was prepared according to the manufacturer's protocols using a collagen gel kit (Cellmatrix I-A, Nitta gelatin). 250 µl of the reagent was developed over each of the cell culture substrates on a culture container and then the substrates were maintained at room temperature for 10 minutes for gelling to some extent. The cell culture substrate was placed on the collagen gel, so that the cell patch arrays faced the collagen gel. Under the condition, the substrate was allowed to stand within an incubator at 37° C. for 3 minutes. The above medium was added and then cells were cultured for 4 hours within the incubator. At this time point, almost no cells of the cell array patches migrated. Subsequently, the substrate was carefully peeled off using a pair of tweezers and then the cell patch arrays were transferred onto the collagen gel. The medium was then removed by suction. 250 µl of the collagen reagent was added to each substrate. The substrate was allowed to stand within the incubator for 30 minutes for gelling of collagen. Subsequently, medium was added and then three-dimensional culture was performed with the configuration of FIG. 2. When observed under a phase-contrast microscope, cells in the periphery of the cell patches initiated migration after 4 hours of culture. 14 hours later, the cells further migrated but cells in the patch central portions migrated only slightly. 40 hours later, cells further migrated and proliferated, so that cell patches seemed to be connected with each other. Moreover, the cells in the patch central portions became almost spindle-shaped unlike the original shape at the initiation of three-dimensional culture. Furthermore, 10 µM dimethylsulfoxide (DMSO) was added and then similar three-dimensional culture was performed and an experiment was conducted without using DMSO. When the results of the two experiments were compared, there were no significant differences in terms of change over time in cell motility. These results demonstrated that the effects of various inhibitors can be tested using these experiments as control experiments.

Example 6

Cell Culture

A substrate for pattern culture used herein was prepared by forming 300-µm square cell adhesion regions prepared in Example 5 at a pitch of 600 µm. Cells and medium same as those used in Example 5 were used. 4×10$^5$ normal human (adult) dermal fibroblasts (NHDF) were seeded per substrate, an appropriate amount of medium was added, and then cells were cultured within an incubator. 23 hours later, when observed under a phase-contrast microscope, cell spheroid arrays were formed. Furthermore, $1.8 \times 10^5$ NHDFs were seeded per substrate, so that cell patch arrays were prepared.
(Embedding of Cell Aggregate into Gel)

The above cell spheroid arrays and cell patch arrays were embedded into gel that had been prepared from the collagen gel kit used in Example 5. Three-dimensional culture was performed with the configuration of FIG. 1. Cell movement and cell proliferation were observed over time. As a result of this experiment, in the case of the cell spheroid arrays, the cells in the regions that had initially adhered to the pattern culture substrate were the first cells that began their migration. In terms of cell migration distance per unit time, there were no significant differences between the cells in the regions that had initially adhered to the pattern culture substrate and the cells in the periphery of the patches of the cell patch arrays. On the other hand, spheroids' own migration was not observed for at least approximately 15 hours after the initiation of culture. At 40 hours after the initiation of culture, the density of spheroids' main bodies became lower and cell infiltration from the spheroids' main bodies was observed.

Example 7

Substrate Preparation for Cell Culture (First-Step Reaction)

A solution was prepared by mixing 39 g of toluene, 13.5 g of epoxysilane (TSL8350, GE Toshiba Silicone), and 450 µl of triethylamine. A predetermined amount of the thus prepared solution was transferred into a glass Petri dish. A glass plate having a diameter of 31 mm and a thickness of approximately 0.1 mm, which had been washed with ultraviolet rays, was immersed in the solution, followed by 18 hours of reaction at room temperature. The glass plate was washed with ethanol, subjected to ultrasonic washing with water, and then dried. The water contact angle of the glass plate surface was 51.1° on an average.

(Second-Step reaction)

25 µl of concentrated sulfuric acid was added to 50 g of tetraethylene glycol while stirring. A predetermined amount of the solution was transferred to a glass Petri dish. The above epoxidized glass plate was immersed in the solution, followed by 20 minutes of reaction at 80° C. After reaction, the substrate was washed with water and then dried. The water contact angle of the surface was measured. The water contact angle was 30.2° on an average.

(Oxidation Treatment and Preparation of Patterning Bottom Dish)

Patterning glass was obtained by 180 seconds of exposure under the conditions same as those in Example 4 and oxidation treatment following thereto. The glass was attached onto the underside of a 35-mm polystyrene dish with a hole having a diameter of 27 mm, so that the hole was covered with the glass.

(Cell Culture)

The above dish was sterilized with 70% ethanol. Normal human (adult) dermal fibroblasts (KF-4109, Cascade Biologics) dispersed in a culture solution (basal medium M-106-500S, additive agent KE-6350, and Cascade Biologics/KURABO) was seeded at $4 \times 10^5$ cells per dish. Cells were cultured using an incubator under conditions of 37° C. and 5% $CO_2$ for 18 hours. A linear pattern formed by cells that had adhered was obtained.

(Embedding of Cell Aggregate into Gel)

Cell aggregates were embedded into gel that had been prepared using the collagen gel kit used in Example 5 and then three-dimensional culture was performed with the configuration of FIG. 3. After 30 minutes of gelling at 37° C., three types of culture were performed using (1) a system containing the above culture solution, (2) a system containing a culture solution prepared by adding 10 µM inhibitor PP2 to the above culture solution, and (3) a system containing a culture solution containing DMSO with the same concentration as that of DMSO (used as a solvent for preparing 1 mM stock solution of PP2) contained in the above-prepared culture solution containing PP2. Cell migration and cell proliferation conditions were observed at 3 hours, 6 hours, 9 hours, and 21 hours after the initiation of culture. As a result, cell migration and cell proliferation were significantly suppressed in the system (2) containing the inhibitor, compared with the systems (1) and (3).

Example 8

Cell Culture

Substrates for pattern culture (200 µm-square cell adhesion regions were formed at a pitch of 400 µm) that had been used in Example 5 and cut in advance were subjected to high-pressure vapor sterilization using an autoclave. These substrates were arranged in culture containers. BAEC was pattern-cultured using MEM medium containing 5% fetal calf serum. The following three-dimensional culture was performed using the substrate on which pattern culture had been performed for 18 hours and the substrate on which pattern culture had been performed for 42 hours and cell-to-cell adhesion had been further developed.

(Embedding of Cell Aggregate into Gel)

With the use of Growth Factor Reduced (GFR) Matrigel (Becton, Dickinson and Company), three-dimensional culture was performed with the configuration of FIG. 3 similarly to Example 2. Time lapse observation was performed. As a result, there were no significant differences between the system involving 18 hours of pattern culture and the system involving 42 hours of pattern culture in terms of the random nature of cell movement and the average cell movement velocity. In contrast, there was a significant difference between the two in terms of increasing amount (of area S enclosing the cell population) per unit time. Specifically, the increasing amount (of area S in the system involving 42 hours of pattern culture) per unit time was ⅕ with respect to that of the system involving 18 hours of pattern culture. This may be due to compositive effects of cell-to-cell adhesion strength of vascular endothelial cells, shrinkage force of cell aggregates, and differentiation and/or dedifferentiation of vascular endothelial cells.

What is claimed is:

1. A biological test kit, wherein said test kit comprises (a) a culture instrument having a culture surface on which a cell pattern can be formed, and (b) a gel suitable for embedding said cell pattern, wherein said culture surface comprises a cell adhesion region and a cell-adhesion-inhibiting region, and wherein said cell adhesion region is formed by subjecting a cell-adhesion-inhibiting hydrophilic film containing an organic compound having a carbon-oxygen bond to oxidation treatment and/or degradation treatment, so that when said culture surface is coated with said gel thereby embedding said cell pattern into said gel, said culture instrument can be peeled off the gel.

2. The biological test kit according to claim 1, wherein the culture surface of the culture instrument is provided with a cell adhesion region and a cell-adhesion-inhibiting region, the cell adhesion region and the cell-adhesion-inhibiting region are each formed with a hydrophilic film containing an organic compound having a carbon-oxygen bond, and the density of the organic compound in the cell adhesion region is lower than that of the organic compound in the cell-adhesion-inhibiting region.

3. The biological test kit according to claim 1, wherein the difference in height between said cell adhesion region and said cell-adhesion-inhibiting region is 10 nm or less.

4. The biological test kit according to claim 1, wherein the gel is selected from the group consisting of a hydrophilic polymer, a hydrogel made of an artificial peptide, a gel made of a polysaccharide, a gel made of a protein, an extracellular matrix, and a gel made of complexes thereof.

5. The biological test kit according to claim 1, wherein the cell-adhesion-inhibiting hydrophilic film is formed by a main raw material selected from the group consisting of polyalkyleneglycol, polyacrylic acid, polymethacrylic acid, polyacrylamide, polyvinyl alcohol, a zwitterionic polymer, a polysaccharide; an alkylene glycol oligomer, an acrylate oligomer, a methacrylate oligomer, an acrylate oligomer, a saponifiable substance of a vinyl acetate oligomer, an oligomer comprising zwitterionic monomers, acrylic acid, methacrylic acid, acrylamide, a zwitterionic compound, a water-soluble silane coupling agent, a water-soluble thiol compound and a derivative thereof.

* * * * *